United States Patent [19]

Brois et al.

[11] 4,017,406

[45] Apr. 12, 1977

[54] CARBOXYLATE HALF ESTERS OF 1-AZA-3,7-DIOXABICYCLO[3.3.0] OCT-5-YL METHYL ALCOHOLS, THEIR PREPARATION AND USE AS ADDITIVES FOR OLEAGINOUS COMPOSITIONS

[75] Inventors: Stanley J. Brois, Wantage, England; Jack Ryer, East Brunswick; Esther Winans, Colonia, both of N.J.

[73] Assignee: Exxon Research and Engineering Company, Linden, N.J.

[22] Filed: May 1, 1975

[21] Appl. No.: 573,545

[52] U.S. Cl. .................... 252/51.5 A; 252/51.5 R
[51] Int. Cl.² ...................................... C10M 1/32
[58] Field of Search ................. 252/51.5 R, 51.5 A

[56] References Cited

UNITED STATES PATENTS

| 3,455,831 | 7/1969 | Davis | 252/51.5 A |
| 3,455,832 | 7/1969 | Davis | 252/51.5 A |

*Primary Examiner*—Delbert E. Gantz
*Assistant Examiner*—Andrew H. Metz
*Attorney, Agent, or Firm*—Roland A. Dexter; Frank T. Johmann

[57] ABSTRACT

Ester derivatives of 1-aza-3,7-dioxabicyclo [3.3.0] oct-5-yl methyl alcohols which are the reaction products of organic acid materials, preferably long chain dicarboxylic anhydrides such as octadecenyl and polyisobutenylsuccinic anhydrides and aldehyde/tris [hydroxymethyl] aminomethane (THAM) adducts or mixtures are oleaginous compositions which feature activity in gasoline as rust inhibitors and carburetor detergents; in automatic transmission fluids as friction modifiers and rust inhibitors; and, in automotive, industrial and lubricating oils as sludge dispersants, rust-inhibitors, friction modifiers and copper alloy corrosion inhibitors, the particular use depending on the molecular weight of the ester.

12 Claims, No Drawings

CARBOXYLATE HALF ESTERS OF 1-AZA-3,7-DIOXABICYCLO[3.3.0] OCT-5-YL METHYL ALCOHOLS, THEIR PREPARATION AND USE AS ADDITIVES FOR OLEAGINOUS COMPOSITIONS

BACKGROUND OF THE INVENTION

1. Field of the Invention

The invention relates to novel oil soluble esters derived from the reaction of organic acid materials such as dicarboxylic acids or anhydrides and an aldehyde/tris-(hydroxymethyl) aminomethane adduct or mixture. These novel oil soluble esters have utility as additives for oleaginous compositions and systems including gasoline, automatic transmission fluids and lubricating oils and as synthetic lubricants, per se.

2. Description of the Prior Art

Lubricant and fuel additives derived from hydrocarbon substitutes succinic anhydride, e.g., polyisobutenylsuccinic anhydride, with compounds containing both an amine group and a hydroxy group have been suggested or investigated in the prior art. For example, U.S. Pat. No. 3,272,746 teaches the reaction of ethanolamine and diethanolamine, as well as various hydroxyalkyl substituted alkylene amines, such as N-(2-hydroxyethyl) ethylene diamine, N,N'-bis(2-hydroxyethyl) ethylene diamine, with alkenylsuccinic anhydride to obtain ashless dispersants for lube oil. U.S. Pat. No. 3,324,033 shows a hydroxy amine, such as diethanolamine reacted with a long chain alkenyl-succinic anhydride to form a mixture of esters and amides, wherein some of the diethanolamine reacts through a hydroxy group to give an ester linkage, while another portion of the diethanolamine forms an amide linkage. U.S. Pat. No. 3,364,001 teaches a tertiary alkanolamine reacted with an alkenylsuccinic anhydride to form an ester useful as a gasoline additive. U.S. Pat. No. 3,448,049 teaches dispersants, corrosion inhibitors and antiwear agents in lubricants and fuels by esterifying alkenylsuccinic anhydride with a hydroxy compound made by reacting an alkanolamine with an unsuaturated ester, amide or nitrile. U.S. Pat. No. 3,630,904 teaches reacting a hydroxy amine, with both short and long chain discarboxylic acid. U.S. Pat. No. 3,484,374 teaches the polymeric condensation products of polycarboxylic acid or anhydride with various alkanolamines such as aminoethyl-ethanolamine, N-methyldiethanolamine, etc. United Kindom Specification 809,001 teaches corrosion inhibitors comprising a multiple salt complex derived from the reaction product of hydrocarbyl substituted dicarboxylic acids and hydroxy amines (including 2-amino-2-methyl-1,3-propane-diol [AMP] and tris hydroxy methylaminomethane (hereafter designated THAM) further complexed with mono- and polycarboxylic acids.

U.S. Pat. No. 3,756,743 teaches reacting polyisobutenylsuccinic anhydride with a polyol, such as pentaerythritol, followed by reaction with THAM. U.S. Pat. No. 3,632,511 teaches reacting polyisobutenylsuccinic anhydride with both a polyamine and a polyhydric alcohol including THAM. U.S. Pat. No. 3,679,428 teaches reacting polyisobutenylsuccinic anhydride with a mixture of pentaerythritol and THAM. United Kingdom Specification 984,409 teaches ashless, amide/imide/ester type lubricant additives prepared by reacting an alkenylsuccinic anhydride, with a hydroxy amine including THAM.

In British Pat. No. 564,506, the condensation product of THAM and formaldehyde, i.e. 1-aza-3,7-dioxabicyclo [3.3.0] oct-5-yl methyl alcohols is said to react with fatty acids to give unstable ester products which are useful as drying oils.

In contrast to the above disclosures, we have found that carboxylic acids or anhydrides can be treated with an aldehyde-THAM adduct or mixture to give novel compositions useful in an unusually wide spectrum of additive applications.

SUMMARY OF THE INVENTION

It has now been discover that novel oil soluble ester derivatives of 1-aza-3,7-dioxabicyclo[3.3.0] oct-5-yl methyl alcohols can be formed from the reaction of organic acids, preferably, dicarboxylic acids and anhydrides, with an aldehyde-(THAM) adduct or aldehyde-(THAM) mixture. For oleaginous compositions wherein the ester compositions of the invention have been found to be highly useful as anti-rust additives, dispersants, and friction modifiers, the preferred aliphatic chain of the carboxylic acid has from about 6 to about 300, optimally from about 12 to about 150, carbons. The aliphatic hydrocarbyl chain can be branched and can possess unsaturation. For applications of the additive compounds in gasoline, the carbon chain length is preferably from about 12 to about 40 to 50 carbon atoms, whereas for applications in lubricating oils it is preferably from about 40 to about 300 carbon atoms, e.g. 60 to 150.

ACID MATERIALS

Numerous types of acid materials can be utilized according to this invention, however mono- and dicarboxylic acids which afford oil soluble esters from aldehyde/THAM adducts or mixtures are preferred. These include mono-car- boxylic acids such as palmitic, stearic, phenylstearic, isostearic, oleic, linoleic and higher molecular weight monocarboxylic acid which can be conveniently formed from the reaction of acrylic acid with polyolefins or with chlorinated polyolefins. Especially preferred reactants are di-carboxylic acid materials, particularly aliphatic substituted succinic acid anhydrides.

Any 2-aldyl, 2-alkenyl-, 2,3-dialkyl or 2,3-cycloalkenyl substituted dicarboxylic acid material, i.e. acid, anhydride or ester e.g., succinic acid anhydride or its corresponding acid, or mixtures thereof can be used in the present invention. The alkyl or alkenyl group can be branched or straight chain, and there is no real upper limit to the number of carbon atoms therein.

It is particularly preferred that the aliphatic substituent in the 2-position of the succinic anhydride is a polymer of $C_2$ to $C_5$ monoolefins, e.g., ethylene, propylene, butylene, isobutylene and pentene. The polymers can be homopolymers such as polyisobutylene and styrene as well as copolymers of two or more of monoolefins such as copolymers of ethylene and propylene, butylene and isobutylene or of propylene and isobutylene. Still other copolymers than can be used include those in which one of the monomers is a diolefin, e.g., a copolymer of isobutylene and butadiene or a copolymer of ethylene, propylene and 1,4-hexadiene.

The polymers will have average molecular weights within the range of about 500 and about 100,000, or moreusually between about 800 and about 20,000.

Particularly useful olefin polymers have average molecular weights within the range of about 900 and about 3000 with approximately one double bond per polymer chain. An especially valuable starting material for a highly potent dispersant additive made in accordance with this invention is polyisobutylene having an average molecular weight in the range of about 900 to about 2300. Molecular weights are conveniently determined by vapor phase osmometry; said determinations being used for all values set forth herein.

Especially useful when it is desired that the additives also possess viscosity index improving properties are 25,000 to 100,000 average molecular weight terpolymers of ethylene-propylene and a diene, e.g., a terpolymer of 25 to 75 weight percent propylene, 2 to 9 percent of a diene such as 1,4-hexadiene, dicyclopentadiene.

The substituted succinic anhydrides are readily available from the reaction of maleic anhydride with polyolefins or with chlorinated polyolefins. Interaction of polyolefins with maleic anhydride [ene reactions] gives polyalkenylsuccinic anhydrides. The olefin polymer can, if desired, be first halogenated, for example, chlorinated or brominated to about 2 to 5 wt. % chlorine, or about 4 to 8 wt. % bromine, based on the weight of polymer, and then reacted with the maleic anhydride (see U.S. Pat. No. 3,444,170).

Other halogenation techniques for attaching the dicarboxylic acid material to a long hydrocarbon chain, involve first halogenating the unsaturated dicarboxylic acid material and then reacting with the olefin polymer, of by blowing halogen gas, e.g. chlorine, through a mixture of the polyolefin and unsaturated dicarboxylic acid material, then heating to 150° to 220° C. in order to remove HCl gas, e.g., see U.S. Pat. No. 3,381,022 and 3,565,804.

In summary therefore, the dicarboxylic acid material used in the invention includes alpha-beta unsaturated $C_4$ to $C_{10}$ dicarboxylic acid or anhydrides or esters thereof such as fumaric acid, itaconic acid, maleic acid, maleic anhydride, malic acid, maleamic acid, chloromaleic acid, dimethyl fumarate, etc. These dicarboxylic acid materials are substituted with a hydrocarbon chain containing at least about 2 carbons to more than 300 carbons, preferably from about 12 to about 150 depending upon the nature of composition into which the additive will be incorporated, that is, for oleaginous compositions such as gasoline, the carbon chain length ranges from 12 to 70 carbons, for automatic transmission fluids the carbon chain length of the hydrocarbyl portion ranges from 12 to 24 carbons and for the lubricating oil composition, it would range from 12 to 300 carbon atoms.

As earlier stated, numerous acids can be reacted with aldehyde/THAM adducts or mixtures. These acids are illustrated by the following types: aromatic acids such as benzoic, phthalic, mellitic and pyromellitic; thioacids such as tridecanethionic, tridecanethiolic and tridecanethionothiolic, heterocyclic acids such as furoic and thienoic acid.

ALDEHYDE-THAM ADDUCTS

The requisite aldehyde/THAM adducts, more specifically 1-aza-3,7-dioxabicyclo[3.3.0] oct-5-yl methyl alcohols (I), can be readily prepared by condensing two moles of aldehyde with one mole of THAM (Equation 1) according to the procedures described by M. Senkus in the Journal of the American Chemical Society, 67, 1515 (1945).

Equation 1

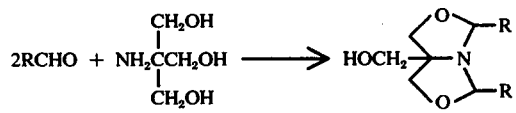

R = H, $CH_3$, n-$C_3H_7$, n-$C_5H_{11}$, Ph, $PhCH_2$, etc.

[I]

Thus, a variety of aldehydes such as formaldehyde, acetaldehyde, propionaldehyde, butyraldehyde, isobutyraldehyde, 2-ethylhexanal, dodecyl aldehyde, benzaldehyde, tolualdehyde, anisaldehyde, piperonal, naphthaldehydes, phenylacetaldehyde, furfural, etc., can be condensed with (THAM) to produce symmetrically substituted (I, R=R) aldehyde/THAM adducts.

UNSYMMETRICAL ADDUCTS

In another embodiment of the present invention, unsymmetrical adducts may be prepared by first treating THAM with one mole of an aldehyde or ketone (Equation 2) to generate an oxazolidine product (II) according to procedures described in the literature by E. D. Bergmann, Chemical Reviews, 53, 309 (1953).

Equation 2

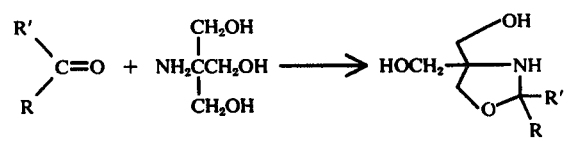

Subsequent treatment of the oxazolidine with a mole of aldehyde affords the unsymmetrical adduct III, as depictured in Equation 3.

Equation 3

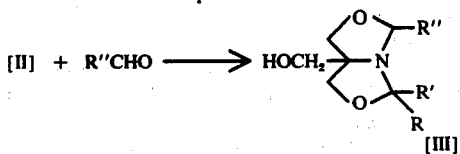

Aldehyde reactants described in the preparation of symmetrically substituted adducts (I) above are suitable for the reactions described in Equations 2 and 3.

Numerous types of ketone reactants can be employed in the formation of the oxazolidines (Equation 2) required in the design of unsymmetrically substituted 1-aza-3,7-dioxabicyclo[3.3.0] oct-5-yl methyl alcohols (III). Included in the repertory of useful ketones are acetone, butanone, pentanones, methyl isobutyl ketone, pinacolone, amyl methyl ketone, cyclopentanone, cyclohexanone, acetophenone, etc.

Long chain aldehydes and ketones formed in the oxidation of copolymers of ethylene and propylene, butylene and isobutylene, and ethylene, propylene and 1,4-hexadiene can also be employed. The aldehyde and ketone functionalized polymers will have average molecular weights within the range of about 500 to about 100,000.

In forming unsymmetrical adducts (III) from oxazolidine generated from ketone reactants, a particularly preferred aldehyde is formaldehyde which, owing to its favorable steric requirements, rapidly cyclizes the oxazolidine intermediate to the desired bycyclic structure, III (R'=H).

In still another embodiment of the instant invention, it has been discovered that glyoxal reacts with THAM when it is placed together in equimolar concentrations to give a novel cyclic diol structure

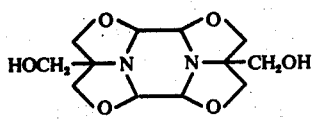

which is hereafter denoted as "glytham". The reaction of "glytham" with carboxylic acid anhydrides leads to esterification of both hydroxyl groups.

REACTION CONDITIONS

The formation of the novel esters of the present invention can be effected by reacting a mole of dicarboxylic acid anhydride with a mole of an aldehyde/THAM adduct i.e. equimolar as portrayed in Eqn. 4.

Equation 4

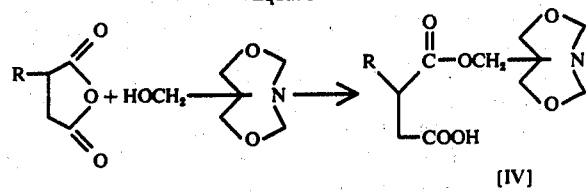

The mode of addition of reactants does not appear to affect product composition, and convenience will usually dictate which reagent is added to the other. Zinc salts such as zinc acetate, chloride, etc. when required, can be employed to catalyze the esterification process. In general, the reaction is effected in a reactor in the absence of or presence of an inert diluent such as xylene and solvent oil and heating the mixture from about 50° C. to about 230° C. preferably 70° C. to 150° C. for about 10 minutes to 48 hours, more preferably 1 to 3 hours. Completion of reaction can be readily discerned by infrared analysis.

The disappearance of the characteristic anhydride carbonyl absorption bands, together with the presence of strong ester and carboxylic acid carbonyl bands indicate that complete esterification has occurred.

In some instances, the half acid ester products (IV) may be further esterified with simple alcohols to afford mixed diesters. Moreover, mono- and polycarboxylic acids and esters can, under certain conditions, be reacted with aldehyde/THAM adducts to give mono and polyesters useful as combustion chamber deposit modifiers and as synthetic lubricants.

In another embodiment of the present invention, the preparation of ester products can sometimes be achieved by simply combining the carboxylic acid or anhydride reactant with a mixture of aldehyde and THAM in the proper molar proportions and heating the well-mixed reagents (neat or in diluent) at about 80° C. to about 220° C. for about 1–24 hours, or until infrared analyses of the mixture indicate that product formation is complete. In such instances, particularly with formaldehyde as reactant, the rate of aldehyde/THAM adduct formation apparently is quite rapid in the presence of the carboxylic acid reactant which at some point, undergoes interaction with the aldehyde/THAM adduct to generate the desired ester.

In a preferred embodiment of the present invention, the symmetrical adduct can be formed in situ, by heating a mixture of 2 moles of aldehyde and a mole of THAM at about 80° C. to about 210° C. for about 1 to about 4 hours. Quite often infrared analysis can be used to discern complete reaction by the disappearance of the aldehyde carbonyl absorption bond. In instances where unsymmetrical adducts are desired, a mole of aldehyde or ketone is heated with a mole of THAM at about 80° C. to about 210° C. for about 1 to about 24 hours, or until periodic infrared analyses of the reaction mixture show the absence of a carbonyl absorption band. Thereafter, a mole equivalent of aldehyde, preferably formaldehyde is added to the intermediary oxazolidine and the mixture is heated at about 80° C. to about 210° C. for approximately 1 to about 4 hours. The insitu formed adduct can thereafter be reacted with a carboxylic acid or anhydride by adding, for example, a mole of alkenylsuccinic anhydride to the adduct and heating the well-stirred reaction mixture at about 80° C. to about 200° C. for approximately 15 minutes to about 4 hours, or until the infrared spectrum of the reaction mixture reveals the absence of the characteristic anhydride carbonyl absorption bands.

The following preparations and examples are included herein as further description and illustrative of the present invention.

PREPARATION OF ALDEHYDE-THAM ADDUCTS

EXAMPLE 1

0.1 mole (12.1 g) of THAM was dissolved in an equal weight of water. To the resulting solution in a 250 ml. Erlenmeyer flask equipped with magnetic stirrer was added 0.2 mole (6.0 g) of paraformaldehyde. The stirred mixture was heated to 70° C. to effect dissolution of the paraformaldehyde and continued for 15 minutes at 70° C. to produce the 1-aza-3,7-dioxabicyclo[3.3.0] oct-5-yl methyl alcohol (hereinafter called DOBO) in quantitative yields. The product after evaporation of water and recrystallization from benzene melted at 60–61° C. and analyzed for 49.12% carbon, 7.52% hydrogen and 9.59% nitrogen.

EXAMPLE 2

1.0 mole (121 g) of THAM was added in one portion to 145 grams of 40% glyoxal in water. As the THAM dissolved the temperature rose from about 25° C. to 35° C. The solution was then stirred at 50° C. for 10 minutes and product began to separate from solution. The mixture was stirred at 50° C. overnight. Filtration afforded a white solid product which weighed 85 g. after drying. Recrystallization from boiling water gave a white solid which melted at 291–292° C. The infrared spectrum of the product as a Nujol mull featured prominent absorption bands at 3.05, 9.38, 9.63, 10.45 and 13.07 microns. The analysis base on $C_{12}H_{18}N_2O_6$ was: Calculated C, 50.34; H, 6.34; N, 9.78, and found C, 50.22; H, 6.32; N, 9.66. The product of this example is hereinafter called "glytham".

ESTERIFICATION OF ALDEHYDE-THAM ADDUCTS

EXAMPLE 3

The bis-acetate ester of "glytham" was formed by refluxing 1 mole of acetic anhydride with 1 mole of glytham using a catalytic amount of zinc chloride salt. The bis-acetate ester melted at 196–197° C. The product ester's infrared spectrum featured strong absorption bands at 5.77, 7.90, 9.27, 9.67 and 13.70 microns. The NMR spectrum of the diester in $CDCl_3$ showed four singlets positioned at 5.21, 5.82, 6.14, and 7.94 tau in the expected intensity ratio. The molecular weight of the bis-acetate ester measured by vapor phase osmometry was 380.

EXAMPLE 4

1-AZA-3,7-DIOXABICYCLO[3.3.0] OCT-5-YL METHYL STEARATE

A 0.1 mole (28.5 g) of stearic acid, 0.1 mole of (DOBO) and 100 ml of xylene were charged into a 500 ml 4-neck round bottom flask equipped with thermometer, stirrer and a Dean Stark moisture trap mounted with a reflux condenser. The mixture was refluxed for about 3 hours. Infrared analyses revealed that esterification was essentially complete, and the solvent was then removed by rotoevaporation. The product (41.2 g) was soluble in heptane and xylene.

EXAMPLE 5

HALF ACID ESTER OF 1-DIOXABICYCLO[3.3.0] OCT-5-YL METHYL OCTADECENYLSUCCINATE 0.5 mole of octadecenylsuccinic anhydride was added to a 1 liter round bottom flask and heated to 140° C. for an hour to convert any partially hydrolyzed reactant to the anhydride form. After cooling the nitrogen-blanketed reactor to 100° C., 0.5 mole of DOBO was added in one portion. The alcohol reagent readily dissolved and the clear solution was heated to 174° C. for about 2 hours. Infrared analysis showed that esterification was complete at this point. The infrared spectrum of the tan product featured prominent absorption bands at 5.75, 5.85, 8.65, 9.10, 10.3 and 10.7 microns. Analysis based on $C_{28}H_{50}NO_6$:
Calculated: C, 67.70; H, 10.15; N, 2.82,
Found: C, 66.57; H, 9.95; N, 2.60, The product, recrystallized from hexane, melted at 58–62° C.

EXAMPLE 6

HALF ACID ESTER OF 1-AZA-3,7-DIOXABICYCLO [3.3.0]OCT-5-YL METHYL POLYISOBUTYLENESUCCINATE 0.2 mole (267 g) of polyisobutenylsuccinic anhydride of MW 980 with a Sap. No. of 84 was charged into a 1 liter flask and heated to 180° C. The anhydride reactant is heated at 180° C. under high vacuum for 2 hours to remove any light ends. About 2.8 g of volatiles were collected in a dry ice-cooled receiver. The stirred reactant is then cooled to 120° C., and 0.2 mole (29.0 g) of DOBO plus 1 gram of zinc acetate catalyst are added. The stirred reaction mixture is then heated at 210° C. for several hours until infrared analysis shows complete esterification. An equal weight of neutral oil (S-150N) is added to the product at about 120° C. The diluted product analyzed for 0.42% nitrogen and featured an infrared spectrum with a dominant absorption band at 5.75 microns.

EXAMPLE 7

0.1 mole (133.5 g) of polyisobutenylsuccinic anhydride of MW 980 with a Sap. No. of ca 84 and 0.1 mole (28.6 g) of glytham were charged into a 500 ml 4-necked round bottom flask. The reaction mixture was blanketed with nitrogen and heated in an oil bath to about 190° C. for 16 hours. The cooled mixture was diluted with 250 ml. of heptane, and filtered. Approximately one-half (16 g) of the glytham was recovered. The filtrate was rotoevaporated to remove solvent and the residue (138 g) was diluted with an equal weight of oil (S-150N). The diluted product featured an infrared spectrum with a strong absorption band at 5.73 microns and analyzed for 0.7% nitrogen.

EXAMPLE 8

HALF ACID ESTER OF 1-AZA-3,7-DIOXA-2,8-DI-N-PROPYL-BICYCLO[3.3.0] OCT-5-YL METHYL OCTADECENYL-SUCCINATE 0.27 mole (94.5 g) of normal octadecenylsuccinic anhydride was added to a 500 ml flask and heated for an hour at 140° C. to convert any partially hydrolyzed reactant to the anhydride form. The reaction was cooled to 70° C. and 0.3 mole (68.7 g) of 1-aza-3,7-dioxa-2,8-di-n-propyl bicyclo [3.3.0] oct-5-yl methyl alcohol was added to the flask and heating was maintained for 1 hour at 98°–104° C. The I.R. spectrum of the product showed disappearance of anhydride bands and the appearance of 2 bands at 5.75 and 5.85 microns.

EXAMPLE 9

HALF ACID ESTER OF 1-AZA-3,7-DIOXA-2,8-DIPHENYL BICYCLO[3.3.0] OCT-5-YL METHYL OCTADECENYL SUCCINATE 0.27 mole (94.5 g) of n-octadecenylsuccinic anhydride was added to a 500 ml. flask and heated for an hour at 140° C. The reaction was cooled to 70° C. and 0.30 moles (89.1 g) of 1-aza-3,7-dioxa-2,8-diphenylbicyclo[3.3.0] oct-5-yl methyl alcohol was added to the flask and heating continued for 1 hour at 107°-114° C. The I.R. spectrum of the product showed the appearance of 2 bands at 5.75 and 5.85 microns.

EXAMPLE 10

HALF ACID ESTER OF 1-AZA-3,7-DIOXABICYCLO[3.3.0] OCT-5-YL METHYL TETRAPROPENYLSUCCINATE 0.8 mole (212.8 g) of tetrapropenylsuccinic anhydride was combined with 0.8 mole (116 g) of DOBO in a 1 liter flask and heated to 138° C. for 2 hours. The product analyzed for 3.2% nitrogen. The calculated value is 3.4%. The I.R. spectrum of the product shows a broad band at about 5.8 microns.

EXAMPLE 11

HALF ACID ESTER OF 1-AZA-3,7-DIOXA-2,8-DI-N-PROPYL-BICYCLO[3.3.0] OCT-5-YL METHYL TETRAPROPENYL SUCCINATE 0.3 mole (79.8 g) of tetrapropenylsuccinic anhydride was reacted with 0.3 mole (68.7 g) of 1-aza-3,7-dioxa2,8-di-n-propyl-bicyclo[3.3.0] oct-5-yl methyl alcohol in a 500 ml flask at 100° C. for 2 hours. The weight percent nitrogen in the product was 2.81%. The calculated value was 2.83%. The IR spectrum of the product showed 2 bands, at 5.75 and 5.85 microns.

EXAMPLE 12

HALF ACID ESTER OF 1-AZA-3,7-DIOXA-2,8-DIPHENYL BICYCLO[3.3.0] OCT-5-YL METHYL TETRAPROPENYL-SUCCINATE 0.2 mole (53.2 g) of tetrapropenylsuccinic anhydride was combined with 0.2 mole (59.4 g) of 1-aza-3,7-dioxa- 2,8-diphenyl-bicyclo[3.3.0] oct-5-yl methyl alcohol in a 500 ml flask and heated to 100°-106° C. for 2 hours. The I.R. spectrum of the product showed 2 bands at 5.75 and 5.85 microns.

EXAMPLE 13

HALF ACID ESTER OF 1-AZA-3,7-DIOXABICYCLO [3.3.0] OCT-5-YL METHYL n-DODECENYLSUCCINATE 0.25 mols (66.8 g) of n-dodecenylsuccinic anhydride was heated at 160°-180° C. for 3 hours with a nitrogen sparge to dehydrate any acid present. It was then cooled to 90° C. and 0.25 moles (38 g) of DOBO in octane was added and the mixture heated 1 hour at 90° C. -110° C. The product showed no anhydride bands in the I.R. spectrum at 5.4 and 5.6 microns and contained 3.7 wt. % nitrogen.

The following example teaches the formation of products via the reaction of an unsymmetrical adduct formed by successive additions of molar amounts of ketone and aldehyde to THAM followed by esterification of the adduct with succinic anhydride.

EXAMPLE 14

A quarter mole of THAM was combined with a half mole of cyclohexanone and the mixture heated at reflux until a clear solution was obtained. The solid product which formed on cooling the solution, was recrystallized from boiling toluene. The dried product, melted at 119°-120° C. and was found to be desired cyclohexanone/THAM adduct, i.e., 2-spiro-(cyclohexyl)-4,4-bis(hydroxymethyl)-oxazolidine. Thirty grams (0.149 mole) of the cyclohexanone/THAM adduct and 5 g (0.166 mole) of paraformaldehyde were added to 150 ml of toluene and the mixture was refluxed in a reactor equipped with a Dean-Stark moisture trap. After 2 hours, approximately 3.1 mole of water were collected and reaction was terminated. Removal of solvent and low ends from the reaction mixture by evaporation afforded 32.1 g of crude product which was homogeneous by gas chromatography. Vacuum distillation gave a colorless viscous liquid which boiled at 159°-160° C. (1.0 mm) and featured infrared and nmr spectra consistent with the unsymmetrical adduct, 1-aza-3,7-dioxa-2-spiro-(cyclohexyl)-5-hydroxymethylbicyclo[3.3.0] octane.

Treatment of 0.1 mole of the unsymmetrical adduct with 0.1 mole of succinic anhydride gave the expected half acid-ester product in high yield.

The above examples teach the preparation of the products of the present invention via the reaction of a carboxylic acid or anhydride, preferably the latter, with a discrete aldehyde/THAM adduct, which is first isolated, purified and characterized (if required), and then employed in a second step involving the esterification of a suitable carboxylic acid or anhydride reagent by the adduct alcohol.

We have also discovered that in certain instances, other synthetic options were also effective and oftimes more convenient in preparing the products of the present invention. One approach involves the addition of a carboxylic acid or anhydride to an aldehyde/THAM adduct which is formed in situ, by simple heating the aldehyde and THAM reagents together as illustrated in Example 15.

EXAMPLE 15

HALF ACID ESTER OF 1-AZA-3,7-DIOXABICYCLO[3.3.0] OCT-5-YL METHYL n-OCTENYLSUCCINAMATE

In a typical reaction, 2 moles (60 g) of paraformaldehyde is added to 1 mole (121 g) of (THAM) and gradually heated with stirring to about 110° C. Heating is continued at 110°-120° C. until a clear solution was obtained. After stirring for 15 minutes, a mole of n-octenylsuccinic anhydride is added to the reactor which is maintained at about 120° C. After the addition of n-octenylsuccinic anhydride is completed, the clear solution is stirred at 120°-130° C. until infrared analysis shows the absence of anhydride bands, e.g. for from about 15 to 30 minutes. Reaction times of 0.25-1 hours, e.g. 15-30 minutes, at 130-140° C. are sufficient to produce the desired ester derivative.

Finally, a second approach which is also operative in certain cases, simply involves the addition of a carboxylic acid or anhydride to the aldehyde and THAM reagents (in the required molar proportions) and heating the resulting mixture until product formation is complete as discerned by infrared analysis. Example 16 describes briefly the experimental details of this approach.

EXAMPLE 16

A mixture comprising a tenth mole of paraformaldehyde, 0.05 mole of THAM and 0.05 mole of n-octenylsuccinic anhydride is gradually heated, with stirring, to about 160°–170° C. for about an hour. The infrared spectrum of the reaction product was virtually identical to that recorded for the product obtained in Example 15.

USE OF THE ESTER ADDITIVE IN OLEAGINOUS COMPOSITIONS

The oil-soluble ester reaction products of this invention can be incorporated into a wide variety of oleaginous compositions. They can be used in lubricating oil compositions, such as automotive crankcase lubricating oils, automatic transmission fluids, etc., in concentrations generally within the range of about 0.01 to 20 weight percent, e.g. 0.1 to 10 weight percent, preferably .3 to 3.0 weight percent, of the total composition. The lubricants to which the ester products can be added include not only hydrocarbon oils from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergents, antirust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers or in turbine oils, about 0.001 to 2 wt. % will generally be used.

The ester additives may be conveniently dispensed as an additive concentrate of from 2 wt. % to 100 wt. % with the balance conventionally a mineral lubricating oil e.g. up to 98 weight percent, with or without other additives being present.

In the above compositions or concentrates, other conventional additives may also be present including dyes, pour point depressants, antiwear agents such as $P_2S_5$-treated terpene or zinc dialkyl dithiophosphates of 3 to 8 carbon atoms in each alkyl group, antioxidants such as N-phenyl-$\alpha$ naphthylamine, tert-octylphenol sulfide, 4,4'- methylene bis(2,6-di-tert-butyl phenol), viscosity index improvers such as ethylene-propylene copolymers, polymethacrylates, polisobutylene, alkyl fumerate-vinyl acetate copolymers and the like, deemulsifiers such as polysiloxanes, ethoxylated polymers and the like. The esters of the invention can also be used as synthetic lubricants.

The invention will be further understood by reference to the following use examples, which include preferred embodiments of the invention.

GASOLINE ADDITIVES

The products of Examples 4, 5, 6 and 9 were tested for their effectiveness as gasoline antirust agents. Each product was first dissolved in xylene and the solutions added to the gasoline to incorporate the additive at a treat rate of 12 pounds of ester additive per thousand barrels of gasoline. The gasoline so treated was then tested for rust according to ASTM D-665M rust test. In brief, this test is carried out by observing the amount of rust that forms on a steel spindle after rotating for an hour in a water-gasoline mixture. In each case, the ester treated gasoline gave no rust indicating that each product was very effective as an antirust additive since the untreated gasoline will form rust over the entire surface of the spindle. The chemical structure of the ester products of the invention and most particularly, the nature of the alkyl or alkylene hydrocarbyl chain of the carboxylic acids determines in part the useful concentration range of the additive to be incorporated into the gasoline. The product of Example 6, for example, broadly is useful at treat rates of 3 pounds to about 35 pounds per thousand barrels of active ingredient and in a preferred range is from about 5 to about 25 pounds and optimally should be about 6 to about 12½ pounds per thousand barrels. This treat range is also suitable for the product of Example 5, whereas for the product of Example 4 a higher treat rate is desired as for example the broad range should be around 3 to about 35 pounds per thousand barrels, but the preferred range is from about 12 to about 25 pounds per thousand barrels and optimally should be from about 15 to about 20 pounds per thousand barrels.

Another application of these additives which has been earlier referenced is their addition to gasoline as a carburetor detergent. Particularly useful as such a detergent is the product of Example 5 which for optimal carburetor detergency is incorporated into the gasoline at a treat rate of about 6 pounds to about 12½ pounds per thousand barrels with about 10 pounds per thousand barrels being the preferred level. If the additive is also desired to impart anti-stall characteristics to the automobile and to the gasoline then the treat rate which is used for carburetor detergency should be about double in order to provide both characteristics, that is a treat rate of the product, for example, Example 6 of about 12½ pounds to about 25 pounds per thousand barrels.

The efficiency of the additive of the invention as carburetor detergencies were made by evaluating the effect of the additive of the invention in comparison with a commercial product consisting of the reaction product of polyisobutenyl succinic anhydride and polyamine, i.e. with the product of Example 6. The treat rate of the gasoline was at a rate of 25 pounds per thousand barrels of the additive of Example 6 with a treat rate of 45 pounds per thousand barrels of the reaction product of polyisobutenyl/succinic anhydride and polyamine. The vehicles which were subjected to test were two 1974 taxis with the product of Example 6 and a 1973 taxi with the commercial additive. The vehicles were Ford, 302 CID, V-8's equipped with emission control hardware. The oil used was SAE 30 SE level. The driving schedule was for a distance of 8000 miles of which 10% was freeway driving, 30% was idle conditions and 60% was stop and go with a mean velocity of about 30 miles per hour. The results of the test shown in Table I were as follows:

TABLE I

| Additive | Carburetor rating (10 = clean) | |
| --- | --- | --- |
| | Initial | Final |
| Prod. Example 6 | 7.2 | 9.9 |
| | 8.4 | 9.7 |
| Commercial | 7.5 | 9.9 |

The results above indicate that the gasoline additive of the invention possesses carburetor detergency comparable to the commercially available additive.

AUTOMATIC TRANSMISSION FLUID ADDITIVE

As earlier indicated, the additives of the invention also have application as friction modifiers. In particular, the product of Example 5 is a useful friction modifier for incorporation into automatic transmission fluids, (ATF) to reduce the component interactions, without deteriorating the frictional properties of the ATF. The ATF lubricants contain many component additives which are typically blended into the lubricating mineral oil at the following range of treating levels.

| Components | Concentration range, vol. % |
| --- | --- |
| V.I. improver | 1–15 |
| Corrosion inhibitor | 0.01–1 |
| Oxidation inhibitor | 0.01–1 |
| Dispersant | 0.5–10 |
| Pour Point depressant | 0.01–1 |
| De-emulsifier | 0.001–0.1 |
| Anti-foaming agent | 0.001–0.1 |
| Anti-wear agent | 0.001–1 |
| Seal swellant | 0.1–5 |
| Friction modifier | 0.01–1 |
| Mineral oil | Balance |

As indicated above, the friction modifier is optimally the reaction product of Example 5. The treat rate is obvious from the above typical formulations which has been blended for the ATF lubricant. A further advantage has developed from using the additives of the invention as friction modifiers for ATF lubricants, i.e. a reduction in the copper corrosiveness of commercial ATF lubricants, after substitution of the commercial friction modifier with an additive of the invention. The following data is illustrative of the copper corrosion inhibition improvement of ATF lubricants.

Two commercial ATF lubricants I and II were examined in the following copper corrosion test in both modified and unmodified form. The copper corrosion test is carried out as follows: A copper specimen 3 × ½ × 1/16 is polished until clean and uniform, washed in hexane, dried and weighed to the tenth of a milligram. 50 cc of the test fluid is placed in a test tube into which the copper bar is immersed, and the test tube thereafter corked with a cork with two ⅛ holes in it. The tube is placed in a 300° C. aluminum block for 72 hours. At the end of the time, the specimen is removed, washed in hexane, rubbed vigorously with paper towel to remove any loose deposits, rewashed and reweighed. Alternatively, the sample may be blown with dry air at 25 cc/min. during the test.

TABLE II

| ATF | Copper Corrosion Tests, mg. lost in 3 days | | |
| --- | --- | --- | --- |
| | ATF I | ATF I | ATF II |
| Lubricant | Air blown | No air blown | No air blown |
| Unmodified | 17.9 | 21.7 | 16.7 |

TABLE II-continued

| ATF | Copper Corrosion Tests, mg. lost in 3 days | | |
| --- | --- | --- | --- |
| | ATF I | ATF I | ATF II |
| Lubricant | Air blown | No air blown | No air blown |
| Modified by removal 0.2 wt. % friction modifier | 18.9 | 21.7 | 13.7 |
| Modified by removal 0.2 wt. % friction modifier and addition of 0.2 wt. % of Prod. Example 5. | 7.2 | 6.5 | 0.7 |

SLUDGE INHIBITION BENCH (SIB) TEST

A number of the additives of this invention were subjected to a Sludge Inhibition Bench (SIB) Test which has been found, after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersant. A quantity of such used oil was acquired by draining and refilling the taxicab crankcase at 1000–2000 mile intervals.

The Sludge Inhibition Bench Test is conducted in the following manner. The aforesaid used crankcase oil, which is milky brown in color, is freed of sludge by centrifuging for 1 hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5, 1 or 2 weight percent, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 25 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

Using the above-described test, the dispersant action of ester additives of the present invention was compared with the dispersing power of a commercial dispersant referred to as PIBSA/TEPA. The PIBSA/TEPA was prepared by reaction of 1 mole of tetraethylene pentamine with 2.8 moles of polyisobutenylsuccinic anhydride obtained from polyisobutylene of about 1000 number average molecular weight. The PIBSA/TEPA dispersant was used in the form of an additive concentrate containing about 50 weight percent PIBSA/TEPA in 50 wt. % mineral lubricating oil. This PIBSA/TEPA additive concentrate analyzed about 1.14% nitrogen, indicating that the active ingredient, i.e., PIBSA/TEPA per se, contained about 2.28% nitrogen. Sufficient quantities of all the additive concentrates tested below were used in making the test blends to furnish the 0.5 and 1.0 weight percent of actual additive. The test results are given in Table III.

TABLE III

SLUDGE DISPERSANCY TEST RESULTS
Milligrams of Sludge In a 10 gram Sample

| Additive of Example | 1.0 wt. % | 0.5 wt. % |
|---|---|---|
| 6 | 0 | 4.82 |
| PIBSA/TEPA | 0 | 1.87 |

The oil without sludge dispersants gave 10 mg. sludge/10 g. of oil as a result of the SIB test. The additive of the invention possesses dispersant activity at concentrations of both 0.5 and 1.0 wt. %.

WARBURG TEST FOR RUST INHIBITION

The Warburg apparatus consists of a temperture controlled flask connected to a capillary manometer with a manometer liquid connected to a large reservoir. The test apparatus has been described by Horner entitled "Uber die Wirkungsweise von Korrosioninhibitoren" in "Werkstoffe Und Korrosion". 23, pp. 466–474 (1972) as a measure of the antirust effectiveness of a number of organic compounds in lubricants. In carrying out the test, 3 grams of iron filings are dispersed in a 10 gram sample of the lubricant to be evaluated for rust inhibition effectiveness. The test sample is heated for about 20 minutes at 50° C. Thereafter 0.75 ml. of 2N HCl is added to the sample. The sample is held at 50° C. with stirring; the oxygen intake is measured after 150 minutes. The additives of the invention exhibited at a concentration of 1.0 wt. % in Solvent 150 Neutral Oil the following rust inhibition values.

| Additive | % Inhibition |
|---|---|
| Example 5 | 82 |
| Example 10 | 68 |
| None | 0 |

Clearly, the additives of the invention exhibit excellent rust inhibition activity in lubricating oils.

The invention in its broader aspect is not limited to the specific details shown and described and departures may be made from such details without departing from the principles of the invention and without sacrificing its chief advantages.

What is claimed is:

1. A lubricating oil composition comprising a major amount of lubricating oil and in the range of about 0.01 to 20 wt. % of an oil soluble ester which is the half ester reaction product of: (a) about 1 molar proportion of a hydrocarbyl substituted $C_4$ to $C_{10}$ dicarboxylic acid or anhydride having about 6 to about 300 carbon atoms per hydrocarbyl group partly esterified with the reaction product of (b) either about 1 or 2 molar proportions of an aldehyde, or one molar proportion of ketone and one molar proportion of aldehyde, reacted with about 1 molar proportion of tris-(hydroxymethyl) aminomethane; said half ester reaction product having a 1-aza-3,7-dioxabicyclo[3,3,0] octyl ring.

2. A composition according to claim 1, wherein said hydrocarbyl substituted acid or anhydride is alkenyl succinic anhydride.

3. A composition according to claim 2, wherein said alkenyl group is a polymer of a $C_2$ to $C_5$ monoolefin.

4. A composition according to claim 1, wherein said hydrocarbyl substituted acid or anhydride is polyisobutenyl succinic anhydride with about 40 to 300 carbon atoms in said polyisobutenyl group.

5. A composition according to claim 1, wherein said hydrocarbyl group contains about 12 to 24 carbon atoms.

6. A composition according to claim 5, wherein said hydrocarbyl substituted acid or anhydride is octadecenyl succinic anhydride.

7. A composition according to claim 5, wherein said hydrocarbyl substituted acid or anhydride is tetrapropenyl succinic anhydride.

8. A composition according to claim 1, wherein said aldehyde is selected from the group consisting of formaldehyde, glyoxal, acetaldehyde, propionaldehyde, butyraldehyde, isobutyraldehyde, 2-ethylhexanol, dodecyl aldehyde, benzaldehyde, tolualdehyde, anisaldehyde, piperonal, naphthaldehyde, phenylacetaldehyde and furfural.

9. A composition according to claim 8, wherein said aldehyde is formaldehyde.

10. A composition according to claim 8, wherein said aldehyde is glyoxal.

11. A composition according to claim 8, wherein said tris-(hydroxymethyl) aminomethane is reacted with one molar proportion of said ketone and then with one molar proportion of said aldehyde, and wherein said ketone is selected from the group consisting at acetone, butanone, pentanone, methyl isobutyl ketone, pinacolone, amyl methyl ketone, cyclopentanone, cyclohexanone and acetophenone.

12. A composition according to claim 1, wherein the amount of said half ester reaction product is about 0.01 to 5 wt. %, and said half ester is the half ester reaction product of octadecenyl succinic anhydride and the reaction product of two molar proportions of formaldehyde with one molar proportion of tris-(hydroxymethyl) aminomethane.

* * * * *